United States Patent
George et al.

(10) Patent No.: US 10,398,727 B2
(45) Date of Patent: Sep. 3, 2019

(54) METHODS FOR THE TREATMENT AND PREVENTION OF ASBESTOS-RELATED DISEASES

(71) Applicant: University of Technology, Sydney, Ultimo, Sydney, New South Wales (AU)

(72) Inventors: Anthony George, Sydney (AU); Jason Ravasini, Sydney (AU)

(73) Assignee: University of Technology, Sydney, New South Wales (AU)

( * ) Notice: Subject to any disclaimer, the term of this patent is extended or adjusted under 35 U.S.C. 154(b) by 0 days.

(21) Appl. No.: 15/528,707

(22) PCT Filed: Nov. 24, 2015

(86) PCT No.: PCT/AU2015/050737
§ 371 (c)(1),
(2) Date: May 22, 2017

(87) PCT Pub. No.: WO2016/081993
PCT Pub. Date: Jun. 2, 2016

(65) Prior Publication Data
US 2017/0258829 A1    Sep. 14, 2017

(30) Foreign Application Priority Data

Nov. 24, 2014   (AU) .............................. 2014904751

(51) Int. Cl.
| | | |
|---|---|---|
| *A61K 9/00* | (2006.01) | |
| *A61K 9/14* | (2006.01) | |
| *A61K 33/06* | (2006.01) | |
| *A61K 33/08* | (2006.01) | |
| *A61K 45/06* | (2006.01) | |

(52) U.S. Cl.
CPC .............. *A61K 33/08* (2013.01); *A61K 9/007* (2013.01); *A61K 9/0019* (2013.01); *A61K 9/14* (2013.01); *A61K 33/06* (2013.01); *A61K 45/06* (2013.01)

(58) Field of Classification Search
CPC ............ A61K 2300/00; A61K 31/4525; A61K 38/193; A61K 38/2013; A61K 38/21; A61K 31/00; A61K 31/454; A61K 45/06; A61K 31/80
See application file for complete search history.

(56) References Cited

U.S. PATENT DOCUMENTS

| | | | |
|---|---|---|---|
| 2005/0100529 A1 | 5/2005 | Zeldis | |
| 2007/0172435 A1 | 6/2007 | Thone | |

FOREIGN PATENT DOCUMENTS

| | | |
|---|---|---|
| BG | 65218 B1 | 8/2007 |
| WO | 2001012221 A1 | 2/2001 |
| WO | WO01/12221 A1 * | 2/2001 ........... A63K 39/385 |
| WO | 2004033044 A1 | 4/2004 |
| WO | 2011065301 A1 | 6/2011 |

OTHER PUBLICATIONS

Ivkovic S, et al. "TMAZ nanoparticles as potential drugs influencing the cellular signal transduction pathways," NSTI ganotech 2005, NSTI Nanotechnology Conference and Trade Show, May 8-12, 2005.
Margeta K, et al. "Immobilization of asbestos fibers on natural zeolite," Proceedings of the 5th Serbian-Croatian-Slovakian Symposium on zeolites, 2013.
Masa Katic et al. "A clinoptilolite effect of cell media and the consequent effects on tumor cells in vitro," Frontiers in Medicine 11:1722-1732, 2006.
Ozesmi M, et al. "Phenotypic characterization of peripheral blood lymphoid cells in people exposed to fibrous zeolite," British Journal of Industrial Medicine 43:830-833, 1986.
Paveli K, et al. "24 medical applications of zeolites," Retrieved from the internet at URL:http://klinobind.com/wp-content/uploads/2003-Medical-Applications-of-Zeolites.pdf, Jan. 1, 2003.
Pavelic K, et al. "Natural zeolite clinoptilolite: new adjuvant in anticancer therapy," Journal of Molecular Medicine 78:408-720, 2001.
Pavelic K, et al. "Immunostimulatory effect of natural clinoptilolite as a possible mechanism of its antimetastatic ability," Journal of Cancer Research and Clinical Oncology, 128:37-44, 2002.
Teimuraz Andronikashvili, et al. "Possibility of application of natural zeolites for medicinal purposes," Bull. Georg. Natl. Acad. Sci. 3:165, 2009.
Thomas JA, et al. "Toxicological assessment of zeolites, Journal of the American College of Toxicology," 11:259-273, 1992.
Zarkovic Neven et al. "Anticancer and antioxidative effects of micronized zeolite clinoptilolite," Journal of Cancer Research and Treatment, 23:1589-1596, 2003.
Supplementary European Search Report for EP15862201.

* cited by examiner

*Primary Examiner* — Audrea B Coniglio
(74) *Attorney, Agent, or Firm* — K&L Gates LLP; Louis C. Cullman; Michelle Glasky Bergman

(57) ABSTRACT

The present invention relates to methods for the treatment or prevention of asbestos related diseases, in particular mesothelioma and asbestosis, and further to methods for the treatment or prevention of asbestos-induced DNA damage. These methods involve administration to a subject in need thereof compositions comprising zeolite or zeolite-like materials such as clinoptilolite.

13 Claims, 14 Drawing Sheets

Epithelial Cells (A549): DNA Gels

| GEL 1 | |
|---|---|
| Lane Treatment<br>1 Untreated<br>2 FIB 1 μg/cm²<br>3 FIB 2.5 μg/cm²<br>4 FIB 5 μg/cm²<br>5 FIB 10 μg/cm²<br>6 CHY 1 μg/cm²<br>7 CHY 2.5 μg/cm²<br>8 CHY 5 μg/cm²<br>9 CHY 10 μg/cm²<br>10 CRO 1 μg/cm²<br>11 CRO 2.5 μg/cm²<br>12 CRO 5 μg/cm²<br>13 CRO 10 μg/cm² | 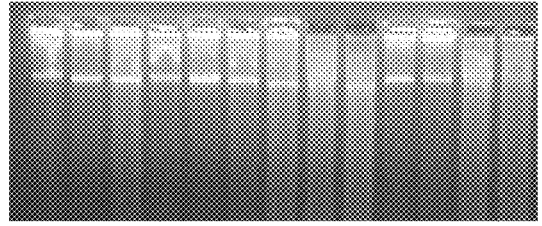 |

FIB = fiberglass  CHY = chrysotile  CRO = crocidolite

| GEL 2 | |
|---|---|
| Lane Treatment<br>1 untreated<br>2 CM 10 μg/cm²<br>3 fibreglass 5 μg/cm²<br>4 fibreglass 5 μg/cm² + CM 10ug/cm²<br>5 chrysotile 5 μg/cm²<br>6 chrysotile 5 μg/cm² + CM 10ug/cm²<br>7 crocidolite 5 μg/cm²<br>8 crocidolite 5 μg/cm² + CM 10ug/cm² | 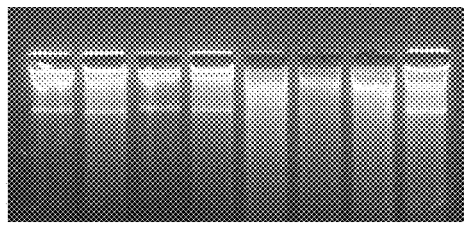 |

| GEL 3 | |
|---|---|
| Lane Treatment<br>1. Untreated<br>2. CM 0.5 μg/cm²<br>3. CM 5 μg/cm²<br>4. CM 10 μg/cm²<br>5. Chrysotile 5 μg/cm²<br>6. Chrysotile 5 μg/cm² + CM 0.5μg/cm²<br>7. Chrysotile 5 μg/cm² CM 5μg/cm² | 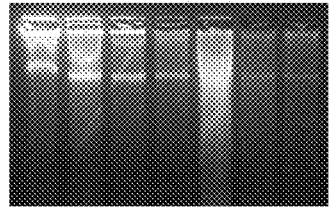 |

Figure 11

METHODS FOR THE TREATMENT AND PREVENTION OF ASBESTOS-RELATED DISEASES

FIELD OF THE INVENTION

The present invention relates to methods for the treatment or prevention of asbestos-related diseases, in particular mesothelioma and asbestosis, and further to methods for the treatment or prevention of asbestos-induced DNA damage.

BACKGROUND OF THE INVENTION

Asbestosis is a chronic lung disease characterised by scarring of lung tissues, which leads to long-term breathing complications. The disease is caused exclusively by exposure to asbestos and there is no cure. Asbestos exposure may also lead to pleural disease which involves inflammation and irritation of the pleura, which is the outer lining of the lung. The pleura stiffens and thickens widely, or in patches (plaques), and can fill with fluid. In some instances this thickening can restrict breathing. Exposure to asbestos fibres also greatly increases a person's risk of developing lung cancer, particularly if the person is a smoker.

Mesothelioma is an aggressive cancer that develops from cells of the mesothelium, the protective lining that covers many of the internal organs of the body. The most common anatomical site for mesothelioma is the pleura (the outer lining of the lungs and internal chest wall), but it may also occur in the peritoneum (the lining of the abdominal cavity), the pericardium (the sac that surrounds the heart), or the tunica vaginalis (a sac that surrounds the testis).

As well as being the cause of asbestosis, it is well known that asbestos is the major cause of mesothelioma and the majority of those who develop mesothelioma have had occupational exposure to asbestos dust or fibres, or were exposed to airborne dust or fibres in other ways. Whilst it has been discontinued in many countries including Australia and the US, asbestos mining continues today in Brazil, China, Russia, India and Kazakhstan with no indications of discontinuence. Occupational exposure to asbestos dust and fibres remains a serious concern for asbestos miners in these countries.

Much of the damage caused by asbestos fibres is due to the cellular uptake of the needle-like fibres. Once inside lung cells, asbestos-bound or released iron generates "cytotoxic" reactive oxygen radicals that cause most of the cellular and DNA damage that leads to asbestosis and mesothelioma. Asbestos may also suppress aspects of the immune system.

Despite chemotherapeutic, radiation and surgical options, patients with mesothelioma face a grim prognosis. Only 12% of patients with negative prognostic factors survive longer than a year. Worldwide, approximately 14,200 people are diagnosed with mesothelioma each year and the incidence of the disease is on the rise in Australia, Europe and Japan. The number of mesothelioma cases is expected to peak worldwide around 2020.

The typical lag of 20 to 40 years between asbestos exposure and the onset of symptoms makes detection, prevention and risk management of asbestos-related disease very difficult. There is therefore a clear and present need for new and effective methods for the treatment and prevention of asbestos-related diseases.

Against this background, the present inventors have developed a method by which mesothelioma and asbestosis may be prevented or moderated in progression or severity.

SUMMARY OF THE INVENTION

In a first aspect the present invention provides a method for treating or preventing an asbestos-related disease in a subject, the method comprising administration to the subject of an effective amount of a zeolite or a zeolite-like material.

In one embodiment the method is a method for preventing an asbestos-related disease in a subject.

The subject may be a subject who is deemed to be at risk of developing an asbestos-related disease.

The subject who is deemed to be at risk of developing an asbestos-related disease may be a subject who currently has, or has previously had, or will in future have, exposure to asbestos. The exposure to asbestos may be, for example, occupational exposure to asbestos.

In one embodiment the subject who is deemed to be at risk of developing an asbestos-related disease may be a subject who will in future have exposure to asbestos. In this embodiment the zeolite or zeolite-like material may be administered before first exposure, during exposure and, optionally, post final exposure. Administration may be daily or weekly.

In another embodiment the subject who is deemed to be at risk of developing an asbestos-related disease may be a subject who currently has, or has previously had, exposure to asbestos. Administration may be daily or weekly.

The method may be a method for treating an asbestos-related disease in a subject. Such methods may further comprise administration of one or more additional therapeutic agents, such as for example, chemotherapeutic agents, immunostimulatory agents or anti-inflammatory agents.

The asbestos-related disease may be mesothelioma, pleural disease, asbestosis or lung cancer.

The asbestos may be chrysotile or crocidolite.

The zeolite or zeolite-like material may be administered in the form of microparticles, for example particles having a mean diameter between about 1 micron and about 5 microns, or having a mean diameter between about 3 microns and about 5 microns.

The zeolite or zeolite-like material may have a cation exchange capacity between about 2.0 and 6.0, or between about 2.0 and 4.0.

The zeolite or zeolite-like material may be a zeolite or zeolite-like material that is capable of binding, entrapping or scavenging Fe ions, preferably $Fe^{2+}$ ions.

The zeolite or zeolite-like material may be a zeolite or zeolite-like material that is capable of overcoming asbestos-induced suppression of the immune system, such as suppression of the macrophage phagocytotic pathway.

The zeolite or zeolite-like material may be a zeolite or zeolite-like material that is capable of stimulating the immune system, such as the Kupffer macrophage phagocytotic pathway.

In some embodiments the zeolite is chabazite, clinoptilolite, ferrierite, boggsite, mordenite, faujasite or any combination thereof. In other embodiments the zeolite is clinoptilolite or chabazite.

The zeolite or zeolite-like material may be administered parenterally, for example intraperitoneally. In alternative embodiments the zeolite or zeolite-like material may be administered via inhalation, for example via oral inhalation.

The zeolite or zeolite-like material may be administered in an amount between about 0.05 mg/kg of body weight and about 1000 mg/kg of body weight, or in an amount between about 1 mg/kg of body weight and about 500 mg/kg of body weight, or in an amount between about 2 mg/kg of body weight and about 400 mg/kg of body weight, or in an amount between about 10 mg/kg of body weight and about 200 mg/kg of body weight, or in an amount between about 20 mg/kg of body weight and about 100 mg/kg of body weight.

The zeolite or zeolite-like material may be administered on a daily, weekly or monthly basis.

In a second aspect the present invention provides a method for treating or preventing DNA damage in a subject, the method comprising administration to the subject of an effective amount of a zeolite or a zeolite-like material.

In one embodiment the method is a method for preventing DNA damage.

The DNA damage may be asbestos-induced DNA damage, for example asbestos-induced lung cell DNA damage.

The subject may be a subject who is deemed to be at risk of sustaining such DNA damage.

The subject who is deemed to be at risk of sustaining such DNA damage may be a subject who currently has, or has previously had, or will in future have, exposure to asbestos. The exposure to asbestos may be, for example, occupational exposure to asbestos.

The zeolite or zeolite-like material may be administered in the form of microparticles, for example particles having a mean diameter between about 1 micron and about 5 microns, or having a mean diameter between about 3 microns and about 5 microns.

The zeolite or zeolite-like material may have a cation exchange capacity between about 2.0 and 6.0, or between about 2.0 and 4.0.

The zeolite or zeolite-like material may be a zeolite or zeolite-like material that is capable of binding, entrapping or scavenging Fe ions, preferably $Fe^{2+}$ ions.

The zeolite or zeolite-like material may be a zeolite or zeolite-like material that is capable of overcoming asbestos-induced suppression of the immune system, such as suppression of the macrophage phagocytotic pathway.

The zeolite or zeolite-like material may be a zeolite or zeolite-like material that is capable of stimulating the immune system, such as the Kupffer macrophage phagocytotic pathway.

In some embodiments the zeolite is chabazite, clinoptilolite, ferrierite, boggsite, mordenite, faujasite or any combination thereof. In other embodiments the zeolite is clinoptilolite or chabazite.

The zeolite or zeolite-like material may be administered parenterally, for example intraperitoneally. In alternative embodiments the zeolite or zeolite-like material may be administered via inhalation, for example via oral inhalation.

The zeolite or zeolite-like material may be administered in an amount between about 0.05 mg/kg of body weight and about 1000 mg/kg of body weight, or in an amount between about 1 mg/kg of body weight and about 500 mg/kg of body weight, or in an amount between about 2 mg/kg of body weight and about 400 mg/kg of body weight, or in an amount between about 10 mg/kg of body weight and about 200 mg/kg of body weight, or in an amount between about 20 mg/kg of body weight and about 100 mg/kg of body weight.

The asbestos may be chrysotile or crocidolite.

The zeolite or zeolite-like material may be administered on a daily, weekly or monthly basis.

In a third aspect the present invention provides use of a zeolite or a zeolite-like material in the manufacture of a medicament for treating or preventing an asbestos-related disease.

In a fourth aspect the present invention provides use of a zeolite or a zeolite-like material in the manufacture of a medicament for treating or preventing DNA damage in a subject.

In a fifth aspect the present invention provides a zeolite or a zeolite-like material for use in treating or preventing an asbestos-related disease.

In a sixth aspect the present invention provides a zeolite or a zeolite-like material for use in treating or preventing DNA damage in a subject.

The medicament may be in a form suitable for inhalation of the zeolite or zeolite-like material.

The medicament may be a medicament suitable for parenteral administration, for example intraperitoneal administration.

In a seventh aspect the present invention provides a method for minimising or modulating asbestos-induced changes in expression of EGR1 or IL-8 in a subject, the method comprising administration to the subject of an effective amount of a zeolite or a zeolite-like material.

In an eighth aspect the present invention provides use of a zeolite or a zeolite-like material in the manufacture of a medicament for minimising or modulating asbestos-induced changes in expression of EGR1 or IL-8 in a subject.

In a ninth aspect the present invention provides a zeolite or a zeolite-like material for use in minimising or modulating asbestos-induced changes in expression of EGR1 or IL-8 in a subject.

The changes in expression may be an increase in expression.

The subject may be a subject who currently has, or has previously had, or will in future have, exposure to asbestos.

Definitions

The following are some definitions that may be helpful in understanding the description of the present invention. These are intended as general definitions and should in no way limit the scope of the present invention to those terms alone, but are put forth for a better understanding of the following description.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In the context of this specification, the terms "a" and "an" are used herein to refer to one or to more than one (i.e. to at least one) of the grammatical object of the article. By way of example, "an element" means one element or more than one element.

In the context of this specification the term "asbestos-related disease" means a disease which is caused by, related to, or in any way associated with, exposure to asbestos or asbestos fibres. The relationship or association may therefore be direct or indirect.

In the context of this specification the term "exposure" as it relates to asbestos exposure encompasses using, working with, or in any way coming into contact with, asbestos or asbestos fibres.

In the context of this specification, the term "about" is understood to refer to a range of numbers that a person of ordinary skill in the art would consider equivalent to the recited value in the context of achieving the same result.

In the context of this specification, the term "effective amount" includes a non-toxic but sufficient amount of a zeolite or zeolite-like material to provide the stated effect. Those skilled in the art will appreciate that the exact amount of zeolite or zeolite-like material required will vary based on a number of factors and thus it is not possible to specify an exact "effective amount". However, for any given case an appropriate "effective amount" may be determined by one of ordinary skill in the art using only routine trial and experimentation.

In the context of this specification, the terms "treating", "treatment", "preventing" and "prevention" refer to any and all uses which remedy the stated disease, disorder or condition, or symptoms thereof, prevent the establishment or onset of the stated disease, disorder or condition, or otherwise prevent, hinder, arrest, retard or reverse the progression of the stated disease, disorder or condition, or other undesirable symptoms in any way whatsoever. Accordingly, the terms "treating", "treatment", "preventing" and "prevention" and the like are to be considered in their broadest possible context. For example, treatment does not necessarily imply that a subject is treated until total and complete recovery.

In the context of this specification, the term "subject" includes humans, primates, livestock animals (e.g. sheep, pigs, cattle, horses, donkeys), laboratory test animals (e.g. mice, rabbits, rats, guinea pigs), companion animals (e.g. dogs, cats), captive wild animals (e.g. foxes, kangaroos, deer), avians and fish. In some embodiments the subject is a human or a laboratory test animal. In other embodiments the subject is a human. In further embodiments the subject is a mammal.

In the context of this specification the term "administering" and variations of that term including "administer" and "administration", include contacting, applying, delivering or providing a zeolite or zeolite-like material to a subject by any appropriate means.

BRIEF DESCRIPTION OF THE DRAWINGS

FIG. 11: DNA gels following treatment of epithelial cells (A549) with fiberglass, chrysotile and crocidolite (Gel 1), CM, fiberglass/CM, chrysotile/CM and crocidolite/CM (Gel 2) and CM, chrysotile and chrysotile/CM (Gel 3). DNA samples of 150 ng/µl (~10 µl/well) were run in 1.2% agarose gels in TBE buffer containing Gel-Red for UV visualization.

DETAILED DESCRIPTION OF THE INVENTION

Figure 1:
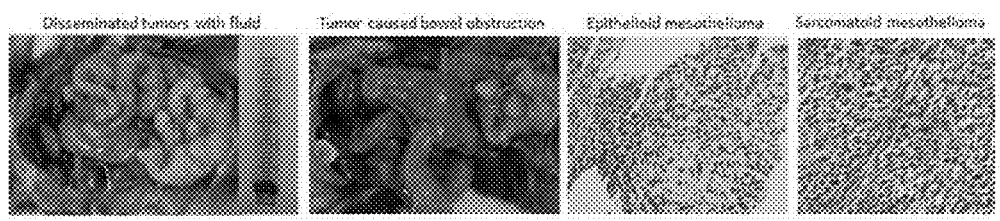
FIG. 1: Different profiles of crocidolite-induced mesothelioma in MexTAg mice following the experiments performed in Example 2.

The present invention is predicated on the surprising finding by the inventors that asbestos-induced cellular and DNA damage, and in particular mesothelioma, may be ameliorated by zeolites. Accordingly, the present invention broadly relates to methods for treating or preventing asbestos-related diseases and to methods for preventing DNA damage utilising zeolites or zeolite-like materials.

Without wishing to be bound by any particular theory, it is suggested that the beneficial effects of zeolite are mediated by stimulation of the immune system (in particular the Kupffer macrophage phagocytotic pathway) and/or by reversing the asbestos-induced suppression of the macrophage immune system and/or by the iron binding/sequestration capability of zeolite which obviates oxidative stress and free radical formation that lead to cellular and DNA damage.

Zeolites are a large group of natural and synthetic microporous hydrated aluminosilicates which are generally regarded as safe (GRAS) by the US Food and Drug Administration (FDA). Zeolite structures are based on a framework of $AlO_4$ and $SiO_4$ tetrahedra which are linked via common oxygen atoms so as to provide a three-dimensional network through which channels run. Each $AlO_4$ group posesses a negative charge which is compensated by a cation, typically a group IA or group IIA element. The cation is able to be exchanged with other cations, such as $Fe^{2+}$. Zeolites used in the methods of the present invention may be natural zeolites or synthetic zeolites.

Zeolite-like materials are materials that have solid structures similar to zeolites and which contain channels with sizes and shapes similar to channel sizes and shapes in zeolite structures. In particular, "zeolite-like materials" may refer to crystalline solids which have zeolite-like structures as indicated by their incorporation in "Atlas of Zeolite Framework Types" by Baerlocher, McCusker and Olsen, Sixth Revised Edition, Elsevier 2007, the content of which is incorporated herein by reference.

Examples of zeolites and zeolite-like materials may also be found in the website of the Structure Commission of the International Zeolite Association (IZA-SC) at the following web address: http://www.iza-structure.org/databases/, the contents of which is also incorporated herein by reference.

Zeolites and zeolite-like materials may be distinguished from denser tectosilicates based on the framework density (FD), which is the number of tetrahedrally coordinated framework atoms (T-atoms) per 1000 Å. The maximum FD for a zeolite or zeolite-like material ranges from 19 to over 21 T-atoms per 1000 Å, depending on the type of smallest ring present, whereas the minimum FD for denser structures ranges from 20 to 22. Accordingly, zeolites and zeolite-like materials suitable for use in the methods of the present invention may have a maximum FD ranging from 19 to 21, 19 to 22, 19 to 23, 19 to 24, 19 to 25, 19 to 26, 19 to 27, 19 to 28, 19 to 29, or 19 to 30 T-atoms per 1000 Å.

In some embodiments the zeolite or zeolite-like material is a zeolite or zeolite-like material that is capable of stimulating the immune system, for example the Kupffer macrophage phagocytotic pathway. In other embodiments the zeolite or zeolite-like material is a zeolite or zeolite-like material that is capable of overcoming asbestos-induced suppression of the immune system, such as suppression of the macrophage phagocytotic pathway. In other embodiments the zeolite or zeolite-like material is a non-fibrous zeolite. In other embodiments the zeolite or zeolite-like material is a zeolite or zeolite-like material which is non-needle-like. The zeolite or zeolite-like material may be other than 4,5 dicyclo, disilico, dimagnesium, dialumino, oxyo, trihydrate, or a salt thereof. The zeolite may be a zeolite that is other than erionite.

Examples of zeolites that may be used in the methods of the invention include, but are not limited to: amicite, analcime, barrerite, bellbergite, bikitaite, boggsite, brewsterite, chabazite, clinoptilolite, cowlesite, dachiardite, direnzoite, edingtonite, epistilbite, faujasite, florkeite, ferrierite, garronite, gismondine, gmelinite, gobbinsite, gonnardite, goosecreekite, harmotome, herschelite, heulandite, laumontite, leucite, kalborsite, levyne, maricopaite, mazzite, merlinoite, mesolite, montesommaite, mordenite, mutinaite, natrolite, offretite, paranatrolite, paulingite, pentasil, perlialite, phillipsite, pollucite, scolecite, stellerite, stilbite, svetlozarite, tetranatrolite, thomsonite, terranovaite, tschernichite, tschortnerite, wairakite, wenkite, wellsite, willhendersonite, yugawaralite including any and all combinations thereof. In some embodiments the zeolite is clinoptilolite or chabizite. In alternative embodiments the zeolite is chabazite, clinoptilolite, ferrierite, boggsite, mordenite or faujasite. The above referenced zeolites may be natural or synthetic zeolites.

In some embodiments the zeolite is clinoptilolite that is commercially available from St Cloud Mining Company, New Mexico, USA. In alternative embodiments the zeolite is a zeolite that is commercially available from Wako Pure Chemical Industries, Ltd, for example a zeolite Y sold under the trade name HS-320 or HS-341, a mordenite sold under the trade name HS-642 or HS-690, a zeolite L sold under the trade name HS-500 or a ferrierite sold under the trade name HS-720.

The zeolite may be a synthetic zeolite which is granular or planar.

Non-limiting examples of zeolite-like materials include kehoeite, pahasapaite, tiptopite, hsianghualite, lovdarite, viseite, partheite, prehite, roggianite, apophyllite, gyrolite, okenite, tacharanite, tobermorite, alfarsenite, ammonioleucite, beaumontite, chiavennite, ferrochiavennite, gaultite, kirchhoffite, nabesite, strontiohurlbutite and weinebeneite.

The zeolite or zeolite-like material may be administered in the form of microparticles, for example particles having a mean diameter between about 0.05 microns and about 25 microns, or between about 0.1 microns and about 15 microns, or between 1 micron and about 10 microns, or between about 2 microns and about 8 microns, or between about 3 microns and about 5 microns, or between about 3 microns and about 10 microns, or between about 3 microns and about 20 microns, or between about 4 microns and about 5 microns, or between about 4.0 microns and about 4.5 microns. In one embodiment, the particles may have a mean diameter of about 4.2 to 4.3 microns.

In some embodiments the zeolite or zeolite-like material may have a cation exchange capacity between about 2.0 and 6.0, or between about 2.7 and 5.4, or between about 2.0 and 4.0. In some embodiments the zeolite or zeolite-like material is a zeolite or zeolite-like material that is capable of binding, entrapping or scavenging Fe ions, preferably $Fe^{2+}$ ions.

The method of the first aspect may find particular application in subjects who are deemed to be at risk of developing an asbestos-related disease, such as mesothelioma or asbestosis. Subjects that may fall into this category include subjects that have previously had any exposure whatsoever to asbestos or asbestos fibres, and in particular prolonged previous exposure to asbestos or asbestos fibres. For example, the subject may be a subject who has had exposure to asbestos or asbestos fibres for at least 1, 2, 3, 4, 5, 6, 7, 8, 9, 10, 11, 12, 13, 14, 15, 16, 17, 18, 19, 20 or more years. The exposure may have been on a daily, weekly or monthly basis, and may have been occupational exposure.

Other subjects who are deemed to be at risk of developing an asbestos-related disease, such as mesothelioma or asbestosis include subjects who will in future have exposure to asbestos, such as for example subjects who have not previously had any exposure to asbestos but will have exposure to asbestos at some time in the future. In such subjects the zeolite or zeolite-like material may be administered on a daily or weekly basis for about 8 weeks, about 7 weeks, about 6 weeks, about 5 weeks, about 4 weeks, about 3 weeks, about 2 weeks or about 1 week prior to first exposure, and then daily or weekly throughout the period of exposure. Administration may also be continued post final exposure for as long as deemed necessary.

Other subjects who are deemed to be at risk of developing an asbestos-related disease, such as mesothelioma or asbestosis include subjects who currently have exposure to asbestos or asbestos fibres. In such subjects the zeolite or zeolite-like material may be administered on a daily or weekly basis commencing as soon as possible and continuing throughout the period of exposure. Administration may also be continued post final exposure for as long as deemed necessary.

In some embodiments the subject who may be deemed to be at risk of developing an asbestos-related disease may be a subject that currently works, has worked, or will in future work: in an asbestos mine, as a professional asbestos removalist or on a property that contains asbestos or asbestos fibres.

As noted above, asbestos mining continues today in countries including Brazil, China, Russia, India and Kazakhstan. Many thousands of people work in these mines and all are at risk of asbestos-related diseases. The method of the first aspect has the potential to protect workers in these mines from developing debilitating asbestos-related diseases such as mesothelioma.

Because of the need to safely remove asbestos-containing materials from houses and buildings, the number of professional asbestos removal services has increased considerably over the years. Like asbestos miners, these professionals are at risk of asbestos-related diseases and may therefore benefit from the method of the invention. Building and home owners who perform their own renovations may also come into contact with asbestos-containing materials and may thus also benefit from the method of the first aspect.

Incidents of asbestosis, pleural disease and mesothelioma have also occurred in subjects who have washed items of clothing contaminated with asbestos fibres. Accordingly, other subjects who may be deemed to be at risk of developing an asbestos-related disease include subjects who share a residence with one or more people who have, or have previously had, or will in future have, any exposure whatsoever to asbestos or asbestos fibres.

Medical professionals, such as oncologists, will be capable of determining whether a given subject is at risk of developing an asbestos-related disease by, for example, questioning the subject in relation to risk factors (such as asbestos exposure) and/or conducting relevant medical examinations and tests.

Successful prevention of asbestos-related diseases may be confirmed utilising diagnostic tools and methods well known to those skilled in the art. Examples of available tools and methods for diagnosing mesothelioma include blood tests such as MESOMARK and SOMAmer panel, imaging tests such as MRI, CT scans, PET scans and X-Ray as well as biopsy. Asbestosis may be diagnosed by considering history of asbestos exposure, symptoms such as shortness of breath and coughing, X-Ray, CT scans, lung function tests and biopsy. Pleural disease may be diagnosed by X-Ray, thoracentesis, MRI, CT scans, PET scans and biopsy. Lung cancer may be diagnosed by X-Ray, sputum cytology, PET scans and biopsy.

In the method of the second aspect the DNA damage may be asbestos-induced DNA damage, for example asbestos-induced lung cell DNA damage. The method of the second aspect may find particular application in subjects who are deemed to be at risk of sustaining DNA damage. Subjects that may fall into this category include those described above in connection with the first aspect, for example subjects that currently have, or have previously had, or will in future have, any exposure whatsoever to asbestos or asbestos fibres.

Administration of zeolites and zeolite-like materials in accordance with the invention to subjects who have been diagnosed with asbestos-related diseases may retard, hinder, arrest or reverse progression of the disease and/or one or more symptoms thereof, and thus may be useful in prolonging the life or quality of life of subjects suffering from such diseases. It is therefore to be understood that the invention relates to prevention and also treatment of asbestos-related diseases.

The zeolites and zeolite-like materials may be used alone in the treatment of asbestos-related diseases, or alternatively in combination with radiotherapy and/or surgery and/or other therapeutic agents, for example chemotherapeutic agents, immunostimulatory agents or anti-inflammatory agents, as part of a combination therapy. The zeolites and zeolite-like materials may, in some embodiments, sensitise mesotheliomal cells or lung cancer cells to other chemotherapeutic agents and/or radiotherapy.

The term "combination therapy" is intended to embrace administration of multiple therapeutic agents in a sequential manner in a regimen that will provide beneficial effects and is intended to embrace administration of these agents in either a single formulation or in separate formulations.

Combination therapy may involve the active agents being administered together, sequentially, or spaced apart as appropriate in each case. Combinations of active agents including the zeolites or zeolite-like materials may be synergistic.

The co-administration of the zeolites or zeolite-like materials with other therapeutic agent(s) may be effected by the zeolites or zeolite-like materials being in the same unit dose form as the other therapeutic agent(s), or the zeolites or zeolite-like materials and the other therapeutic agent(s) may be present in individual and discrete unit dosage forms that are administered sequentially, at the same, or at a similar time. Sequential administration may be in any order as required, and may require an ongoing physiological effect of the first or initial agent to be current when the second or later agent is administered, especially where a cumulative or synergistic effect is desired. When administered separately, it may be preferred for the zeolites or zeolite-like materials and the other therapeutic agent(s) to be administered by the same route of administration, although it is not necessary for this to be so.

In some embodiments, the zeolites and zeolite-like materials may be included in combination therapy with one or more chemotherapeutic agents.

There are large numbers of chemotherapeutic agents that are currently in use, in clinical evaluation and in pre-clinical development, which could be selected for treatment of mesothelioma and lung cancer in combination with the zeolites and zeolite-like materials. Suitable agents which may be used in combination therapies include those listed, for example, in the Merck Index, *An Encyclopaedia of Chemicals, Drugs and Biologicals,* 12th Ed., 1996, the entire contents of which are incorporated herein by reference.

In alternative embodiments the zeolites and zeolite-like materials may be administered with one or more of the following chemotherapeutic agents: adriamycin, taxol, docetaxel, fluorouracil, melphalan, cisplatin, alpha interferon, COMP (cyclophosphamide, vincristine, methotrexate and prednisone), etoposide, mBACOD (methotrexate, bleomycin, doxorubicin, cyclophosphamide, vincristine and dexamethasone), PROMACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP 470, pentosan polysulfate, platelet factor 4, angiostatin, LM 609, SU 101, CM 101, Techgalan, thalidomide, SP-PG and the like.

In alternative embodiments the zeolites and zeolite-like materials may be administered with anti-inflammatory agents, such as for example, corticosteroids.

In accordance with the methods of the invention one or more zeolites or zeolite-like materials may be administered by routes well known to those skilled in the art. In general, the zeolite or zeolite-like material may be administered by the parenteral (for example intraperitoneal, intravenous, intraspinal, subcutaneous or intramuscular), oral, topical or inhalation route. Administration may be systemic, regional or local. In one embodiment, the zeolite or zeolite-like material is administered intraperitoneally. In another embodiment the zeolite or zeolite-like material is administered by inhalation.

In some embodiments the zeolite or zeolite-like material may be administered in the form of a medicament or pharmaceutical composition. Suitable compositions can be prepared according to methods known to those skilled in the art and may include pharmaceutically acceptable carriers, diluents and/or excipients. The carriers, diluents and excipients must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil or coconut oil; silicone oils, including polysiloxanes, such as methyl polysiloxane, phenyl polysiloxane and methylphenyl polysiloxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia and petroleum jelly. Typically, the carrier or carriers will form from 10% to 99.9% by weight of the compositions.

Pharmaceutical compositions may be in a form suitable for administration by injection, in the form of a composition suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, or in a form suitable for parenteral administration, that is, subcutaneous, intramuscular, intravenous or intraperitoneal injection.

For administration as an injectable solution or suspension, non-toxic parenterally acceptable diluents or carriers can include cyclodextrins (for example Captisol®) Cremaphor, Ringer's solution, isotonic saline, phosphate buffered saline, ethanol and 1,2 propylene glycol.

Some examples of suitable carriers, diluents, excipients and adjuvants for oral use include cyclodextrins, cremaphor, peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition, these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethylcellulose, polyvinylpyrrolidone, sodium alginate or acetyl alcohol. Suitable dispersing agents include lecithin, polyoxyethylene esters of fatty acids, such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further comprise one or more emulsifying agents. Suitable emulsifying agents include the dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

Topical compositions may comprise a zeolite or zeolite-like material together with one or more acceptable carriers. Compositions suitable for topical administration include liquid or semi-liquid preparations, such as liniments, lotions, creams, ointments or pastes, and drops suitable for administration to the eye, ear or nose.

Creams, ointments or pastes according to the present invention are semi-solid formulations for external application. They may be made by mixing the zeolite or zeolite-like material in finely divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol, such as propylene glycol or macrogols.

The composition may incorporate any suitable surfactant such as an anionic, cationic or non-ionic surfactant, such as sorbitan esters or polyoxyethylene derivatives thereof. Suspending agents such as natural gums, cellulose derivatives or inoraganic materials such as silicaceous silicas, and other ingredients such a lanolin, may also be included.

In some embodiments the compositions are administered in the form of suppositories suitable for rectal administration of the zeolite or zeolite-like material. These compositions are prepared by mixing the zeolite or zeolite-like material with a suitable non-irritating excipient which is solid at ordinary temperatures but liquid at the rectal temperature and will therefore melt in the rectum to release the zeolite or zeolite-like material. Such materials include cocoa butter, glycerinated gelatin, hydrogenated vegetable oils, mixtures of polyethylene glycols of various molecular weights and fatty acid esters of polyethylene glycol.

The compositions may also be administered or delivered to target cells in the form of liposomes. Liposomes are generally derived from phospholipids or other lipid substances and are formed by mono- or multi-lamellar hydrated liquid crystals that are dispersed in an aqueous medium. Specific examples of liposomes used in administering or delivering a composition to target cells are synthetic cholesterol (Sigma), the phospholipid 1,2-distearoyl-sn-glycero-3-phosphocholine (DSPC); Avanti Polar Lipids), the PEG lipid 3-N-[(-methoxy poly(ethylene glycol)2000)carbamoyl]-1,2-dimyrestyloxy-propylamine (PEG-cDMA), and the cationic lipid 1,2-di-o-octadecenyl-3-(N,N-dimethyl)aminopropane (DODMA) or 1,2-dilinoleyloxy-3-(N,N-dimethyl)aminopropane (DLinDMA) in the molar ratios 55:20:10:15 or 48:20:2:30, respectively, PEG-cDMA, DODMA and DLinDMA. Any non-toxic, physiologically acceptable and metabolisable lipid capable of forming liposomes can be used. The compositions in liposome form may contain stablisers, preservatives, excipients and the like. The preferred lipids are the phospholipids and the phosphatidyl cholines (lecithins), both natural and synthetic. Methods to form liposomes are known in the art, and in relation to this, specific reference is made to: Prescott, Ed., Methods in Cell Biology, Volume XIV, Academic Press, New York, N.Y. (1976), p. 33 et seq., the contents of which is incorporated herein by reference.

The compositions may incorporate a controlled release matrix that is composed of sucrose acetate isobutyrate (SAIB) and an organic solvent or organic solvents mixture. Polymer additives may be added to the vehicle as a release modifier to further increase the viscosity and slow down the release rate. SAIB is a well known food additive. It is a very hydrophobic, fully esterified sucrose derivative, at a nominal ratio of six isobutyrate to two acetate groups. As a mixed ester, SAIB does not crystallise but exists as a clear viscous liquid. Mixing SAIB with a pharmaceutically acceptable organic solvent, such as ethanol or benzyl alcohol decreases the viscosity of the mixture sufficiently to allow for injection. A zeolite or zeolite-like material may be added to the SAIB delivery vehicle to form SAIB solution or suspension formulations. When the formulation is injected subcutaneously, the solvent differs from the matrix allowing the SAIB-drug or SAIB-drug-polymer mixtures to set up as an in situ forming depot.

For administration via inhalation the zeolite or zeolite-like material may be provided in the form of a dry powder and delivered by a dry powder inhaler (DPI). The dry powder may comprise a bulking agent, for example lactose. DPIs are well known to those skilled in the art. The zeolite or zeolite-like material may alternatively be delivered in the form of an aerosol. For example, a mixture of zeolite or zeolite-like material and a lubricating agent may be dispersed in a propellant and placed into an appropriate metered-dose inhaler for delivery intranasally or via oral inhalation. When the zeolite or zeolite-like material is administered via inhalation routes the methods of the invention may further comprise administration of a bronchodilator so as to increase airflow to the lungs of the subject. Non-limiting examples of bronchodilators include salbutamol, pirbuterol, terbutaline, clenbuterol, salmeterol, bambuterol and indacaterol. When the zeolite or zeolite-like material is administered with a bronchodilator each component may be administered at the same time, or sequentially in any order, or at different times so as to provide the desired effect. Alternatively, the components may be formulated together in a single dosage unit.

An effective amount of zeolite or zeolite-like material for any particular subject will depend upon a variety of factors including: the type and severity of the asbestos-related disease; the extent of past, present or future asbestos exposures, the activity of the zeolite administered; the composition in which the zeolite is present; the age, body weight, general health, sex and diet of the subject; the time of administration; the route of administration; the duration of the administration; drugs used in combination or coincidental with the zeolite or zeolite-like material, together with other related factors well known in medicine.

One skilled in the art would, by routine experimentation, be able to determine an effective, non-toxic amount of a zeolite or zeolite-like material, which would be required to achieve the desired outcome. In some embodiments the zeolite or zeolite-like material is administered in an amount between about 0.05 mg/kg of body weight and about 1000 mg/kg of body weight, or in an amount between about 0.05 mg/kg of body weight and about 500 mg/kg of body weight, or in an amount between about 0.1 mg/kg of body weight and about 500 mg/kg of body weight, or in an amount between about 1 mg/kg of body weight and about 500 mg/kg of body weight, or in an amount between about 2 mg/kg of body weight and about 400 mg/kg of body weight, or in an amount between about 5 mg/kg of body weight and about 300 mg/kg of body weight, or in an amount between about 10 mg/kg of body weight and about 200 mg/kg of body weight, or in an amount between about 20 mg/kg of body weight and about 100 mg/kg of body weight. The zeolite or zeolite-like material may be administered on a daily, weekly or monthly basis. In one embodiment, the zeolite or zeolite-like material is administered on a weekly basis.

The present invention is further described below by reference to the following non-limiting examples.

EXAMPLES

Example 1—Zeolite Preparation

The zeolite used in the examples that follow was clinoptilolite obtained from St. Cloud Mining Company, New Mexico, USA and prepared according to the following method:

1. The purchased clinoptilolite was milled as follows:
   9 grams of clinoptilolite powder, 12 ml of water and 25×10 mm diameter $ZrO_2$ balls were ground for 5 minutes in a 80 ml grinding bowl to a final clinoptilolite $d_{50}$<4.28 µm.
2. A stock suspension was prepared using the clinoptilolite obtained following step 1 at a concentration of 750 mg/ml and stored in the fridge.
3. On the injection day the suspension was diluted to 3 mg/ml (for injection at 30 mg/kg) or 9 mg/ml (for injection at 90 mg/kg) using sterilised normal saline, injection volume was 10 ml/kg.

Clinoptilolite prepared in accordance with this example is referred to throughout this document as "CM".

Example 2—Effect of CM on Asbestos-Induced Mesothelioma in MexTAg299 Mice

Background

MexTAg299 transgenic mice are suitable for testing asbestos-induced mesothelioma with 100% incidence. MexTAg mice exposed to asbestos develop cancer that faithfully replicates key features of the pathogenesis of human mesothelioma. The protective effect of compound CM against mesothelioma was tested in a MexTAg mouse model following asbestos exposure.

Materials and Methods

Six MexTAg299 transgenic mice (17-19 weeks old) were subjected to intraperitoneal (i.p.) injection of two doses of 2-3 mg crocidolite (blue) asbestos one month apart (weeks 1 and 4). CM was injected i.p. weekly at either 30 mg/kg (6 mice; 0.6 mg/injection) or 90 mg/kg (6 mice; 1.8 mg/injection) from the beginning of the crocidolite insult (week 1) until post-mortem. Controls were normal saline (0.9%) or CM at 90 mg/kg (3 mice each).

Results

Figure 2:
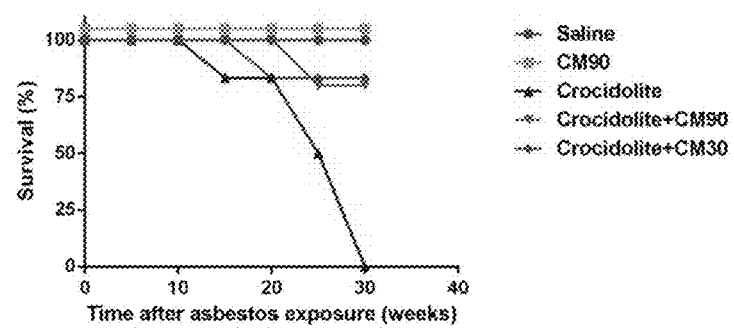
FIG. 2: Plot of percentage mouse survival versus time after asbestos exposure following the experiments performed in Example 2.
Figure 3:
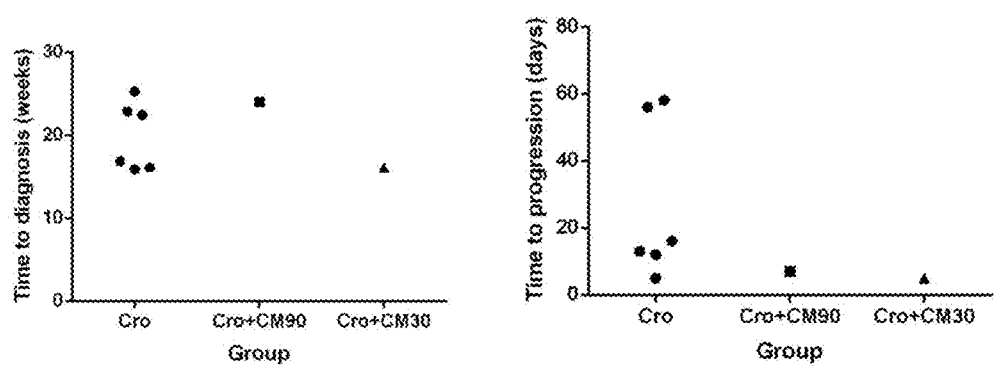
FIG. 3: Plots of time to diagnosis of mesothelioma and time to progression to mesothelioma in the mouse groups that received crocidolite and crocidolite and CM in Example 2.
Figure 4:
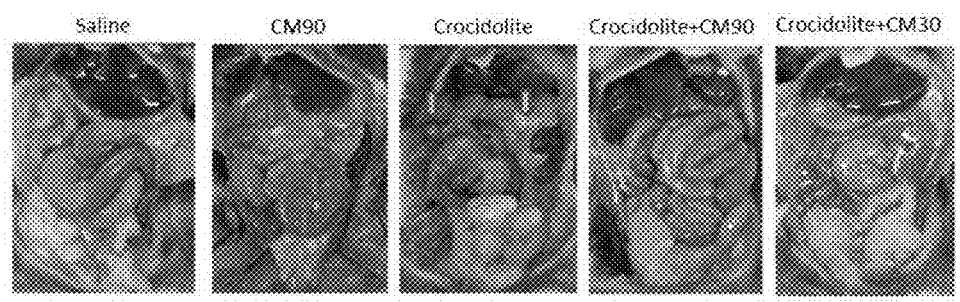
FIG. 4: Mesotheliomal tumours and CM particles distributed in mouse groups following the experiments performed in Example 2. Blue arrows show CM particles and yellow-red arrows show mesotheliomal tumours.

The results are presented in Table 1 below and in FIGS. 1 to 4. Reference to Table 1 shows that mice who received CM at both doses had a drastically reduced occurrence of mesothelioma as compared to mice who received no CM. Reference to FIG. 2 confirms that 30 weeks after asbestos exposure more than 75% of the mice that received CM were alive. Furthermore, reference to FIG. 4 shows that mice that received CM and crocidolite had no visible signs of tumours. All mice who received crocidolite but no CM were dead within 30 weeks of crocidolite exposure. These results clearly demonstrate that CM offers highly effective protection against asbestos-induced mesothelioma.

TABLE 1

CM moderated asbestos-induced mesothelioma incidence and organ damage*

|  | Saline | CM | Crocidolite | Cro + CM90 | Cro + CM30 |
|---|---|---|---|---|---|
| Mice | 3 | 3 | 6 | 6 | 6 |
| Mesothelioma | 0 | 0 | 6 | 1 | 1 |
| Incidence | 0% | 0% | 100% | 16.7% | 16.7% |

*GPower 3.1 analysis at a significance level of 0.5 provides over 80% power to detect the differences between the subgroups using a 2-tailed test (run by Dr Tapan Rai, University of Technology, Sydney)

Liver Histology

Based on post-mortem (macroscopic) examinations of all 24 mice in this example, the liver showed the most obvious changes in morphology and thus liver section cutting and histological staining was performed first.

Figure 5:
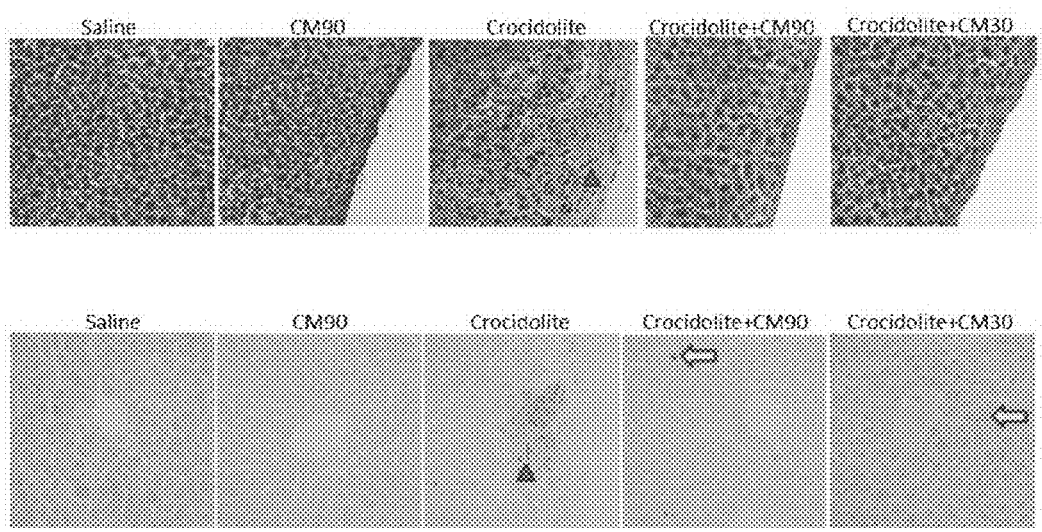
FIG. 5: HE and Prussian blue staining of liver samples of mouse groups following the experiments performed in Example 2 at a magnification of 40×. Blue arrows show crocidolite fibres and yellow arrows show crocidolite fibres inside Kupffer cells.

In the histology, very small liver mesotheliomal tumours were seen under the microscope, and less damaged liver cells were seen after CM treatment (compare the crocidolite HE slide in FIG. 5 with the two crocidolite+CM slides to the right).

Figure 6:
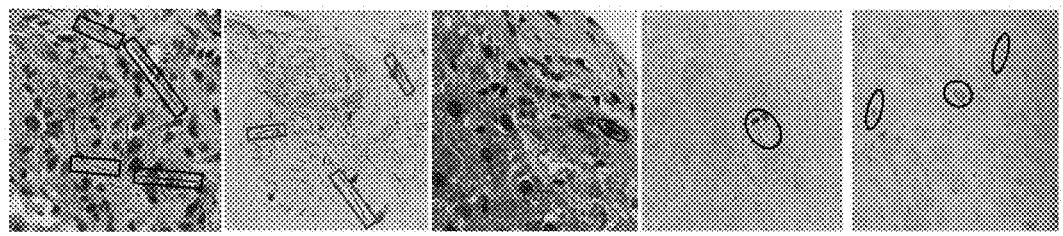
FIG. 6: HE and Prussian blue staining of liver samples of mouse groups following the experiments performed in Example 2 at a magnification of 100×.

In iron staining with Prussian blue, all of the asbestos fibres were located in the peritoneum and liver cells were swollen in crocidolite-treated mice. In the crocidolite+CM mice asbestos fibres were mostly phagocytosed inside liver macrophages (Kupffer cells) with very few asbestos fibres in the peritoneum and far fewer liver cells were damaged. This correlates with the post-mortem macroscopic examinations showing that the livers of asbestos+CM mice were normal in appearance (colour and size). These observations held for all mice examined. Higher magnification (100x) is shown in FIG. 6 with free or phagocytosed fibres more clearly visible than in the 40x slides (FIG. 5).

Macrophage phagocytosis was more prominent in crocidolite+CM30. Interestingly, the histology results suggest that asbestos fibres may inhibit phagocytotic activities thereby exacerbating cell damage and cytotoxic effects, whereas the presence of CM might overcome this effect and enhance macrophage activity and phagocytosis.

In order to better quantify these results, total asbestos fibre counts were made for 16 mice (6 asbestos treated; 5 crocidolite+CM90; and 5 crocidolite+CM30). For each mouse, 10 fields at 40× magnification were counted. The 10 fields covered 80-100% of the liver peritoneum, depending on individual mice.

Figure 7:
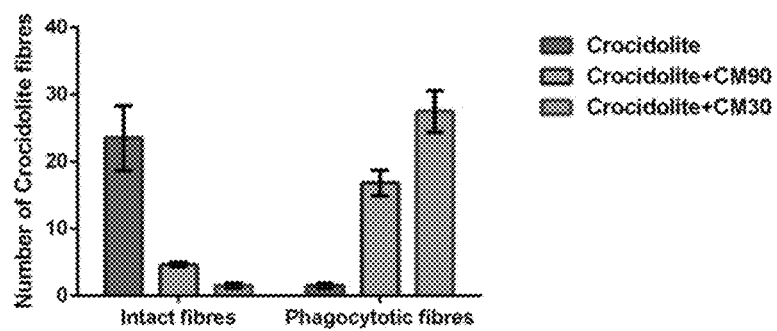
FIG. 7: Total counts of asbestos fibres in the liver peritoneal membrane of mouse groups following the experiments performed in Example 2.

FIG. 7 shows total counts of asbestos fibres in the liver peritoneal membrane. Most asbestos fibres in asbestos-injected mice were freely dispersed in the liver peritoneum (blue bar at left in FIG. 7), while a clear majority of fibres in crocidolite+CM-injected mice were phagocytosed in Kupffer (liver) macrophages (grey and green bars to the right in FIG. 7).

There were very few free asbestos fibres in the 10 crocidolite+CM mice, only several very small blue particles around blood vessels in the liver peritoneum. Kupffer phagocytosis was observed in all crocidolite+CM mice, including—surprisingly—the two crocidolite+CM mice with tumours. However, the number of macrophages was lower in these two mice (14-15 Kupffer cells per section) compared to tumour-free mice (25-35 Kupffer cells per section).

Spleen Histology

Figure 8:
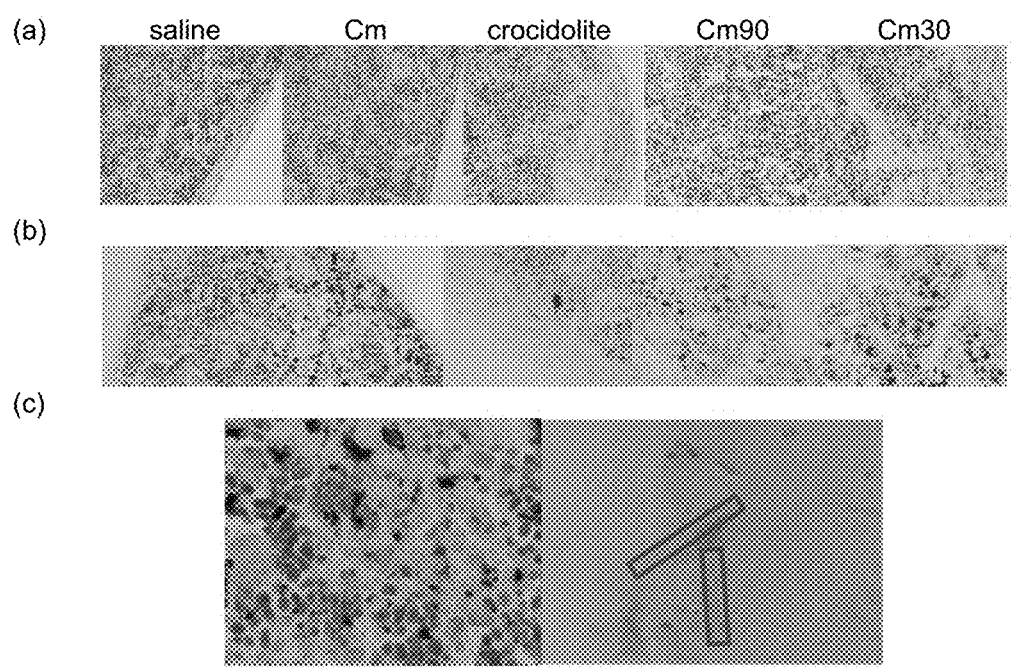
FIG. 8: (a) HE staining of spleen samples of mouse groups following the experiments performed in Example 2 at a magnification of 40×. (b) Prussian blue staining of spleen samples of mouse groups following the experiments performed in Example 2 at a magnification of 40×. (c) Prussian blue staining of spleen samples of mouse groups following the experiments performed in Example 2 at a magnification of 100×.

Staining results are presented in FIG. 8 and were similar to those seen for the liver peritoneal samples, but with a couple of minor differences. First, large amounts of stained iron were observed which is not unexpected because the spleen is engorged with red blood cells. Second, the number of asbestos fibres that were phagocytosed was fewer than that observed in the liver. This is probably because the liver contains its own source of macrophages (as Kupffer cells).

Figure 9:
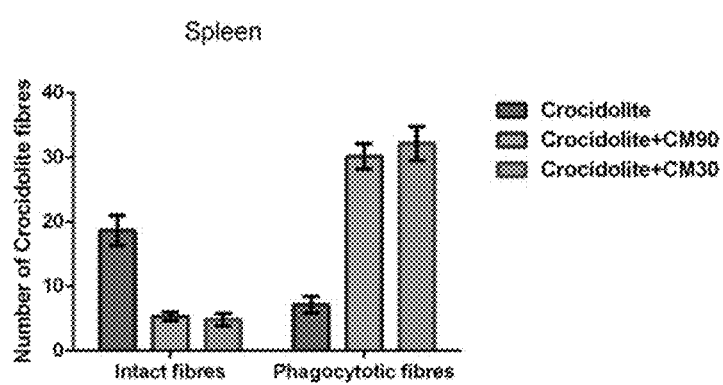
FIG. 9: Total counts of asbestos fibres in the spleen of mouse groups following the experiments performed in Example 2.

The spleen peritoneum samples were quantified in the same way as for the liver results above. Total asbestos fibre counts were made for 18 mice (6 asbestos treated; 6 crocidolite+CM90; and 6 crocidolite+CM30). For each mouse, 10 fields (40×) covering 80-100% were counted. FIG. 9 shows total counts of asbestos fibres in the spleen peritoneal membrane. Most asbestos fibres in asbestos-injected mice were freely dispersed in the peritoneum (blue bar at left in FIG. 9), while a clear majority of fibres in crocidolite+CM injected mice were phagocytosed (grey and green bars to the right in FIG. 9).

Conclusions

Crocidolite-induced mesothelioma incidence can be ameliorated by CM.

CM itself showed no toxic effects or organ or cellular damage at moderate doses (30 to 90 mg/kg injected weekly up to 30 weeks).

One possible mechanism of action of CM involves stimulation of the immune system, in particular the Kupffer macrophage phagocytotic pathway.

Another possible mechanism involves iron binding/sequestration by CM which prevents or minimises oxidative stress and/or failure of the immune pathway.

Example 3—Effect of CM on Asbestos-Induced Mesothelioma in MexTAg299 Mice

Materials and Methods

Six MexTAg299 transgenic mice (17-19 weeks old) were subjected to i.p. injection of two doses of 2-3 mg crocidolite (blue) asbestos one month apart (weeks 1 and 4). CM was injected i.p. weekly at 30 mg/kg (6 mice; 0.6 mg/injection) from the beginning of the crocidolite insult (week 1) until post-mortem, for the first sub-group of mice, which was a repeat of Example 2. 'Cro+Early CM' was for CM injected once weekly, beginning at week 1 along with crocidolite, then stopped at week 10 and the surviving mice observed out to week 30 week. 'Late CM' was for CM injected once weekly, but not beginning until week 10 (with crocidolite as usual given i.p. at weeks 1 and 3), and continued weekly until the end of the trial at week 30 weeks.

Results

The results are presented in Table 2 below. This trial was, in part, an extension of the trial of Example 2. The repeat sub-groups for crocidolite only and crocidolite plus CM at 30 mg/kg showed essentially the same outcome as Example 2, with all 6 mice who received crocidolite but no CM succumbing before week 26 and only 2/6 mice who received crocidolite and CM at 30 mg/kg suffering the same fate. In the case of early (up to week 10) and late (from week 10) weekly CM injections at 30 mg/kg there was excellent survival of mice in both subgroups.

TABLE 2

CM moderated asbestos-induced mesothelioma incidence*

|  | Crocidolite | Cro + CM30 | Cro + Early CM30 | Cro + Late CM30 |
|---|---|---|---|---|
| Mice | 6 | 6 | 6 | 5 |
| Mesothelioma | 6 | 2 | 1 | 2 |
| Incidence | 100% | 33.3% | 16.7% | 16.7% |

*GPower 3.1 analysis at a significance level of 0.5 provides over 80% power to detect the differences between the subgroups using a 2-tailed test (run by Dr Tapan Rai, University of Technology, Sydney)

Example 4—Effect of Asbestos and CM on Gene Expression

Background

Treatment of lung epithelial cells with asbestos in vitro has been shown to induce changes in expression of a number of genes. Alterations in apoptotic, tumour suppressor and inflammatory pathways after exposure to chrysotile and crocidolite asbestos can result in asbestosis and mesothelioma in vivo.

Hevel et al (*BMC Genomics* 2008, 9, 376) identified 43 genes with increased expression and 22 genes whose expression was down regulated after A549 cells were exposed to 6 $\mu g/cm^2$ of crocidolite asbestos for 24 hours.

This experiment sought to replicate these changes in expression and to assess whether these changes, presumably deleterious, were mitigated by co-treatment with CM.

Two genes were chosen from those identified by Hevel et al, based on their high expression in asbestos-treated cells relative to untreated control cells. EGR1 (Early Growth Response 1) showed a 115.7% increase in asbestos-treated cells, whilst IL-8 exhibited a 16.6% increase in expression in asbestos-treated A549 cells.

EGR1 is a transcription factor found in the nucleus. It activates expression of a number of target genes that are involved in the response to various types of cellular stress— TNF-α, TGF-β, ICAM-1, CD44 and PDGF-α and PDGF-β chains (Khachigian and Collins, *Arterioscler. Thromb. Vasc. Biol.* 17: 2280-2286).

IL-8 is a chemokine and inflammatory cytokine produced by various cell types. It is the major neutrophil chemotactic factor in the lung integral to the inflammatory response to foreign particulates such as asbestos fibres.

Method

A549 cells were seeded into either 24-well plates or T25 $cm^2$ flasks to achieve 70% confluence at the time of exposure to asbestos fibres. Initially, cells were treated with a titration of 1-10 $\mu g/cm^2$ asbestos and changes in expression were observed with a dose-dependent response. Concentrations of 5 $\mu g/cm^2$ chrysotile and 10 $\mu g/cm^2$ crocidolite were subsequently chosen as test concentrations against which the mitigating effect of increases in asbestos-induced changes in gene expression in the presence of CM was measured. The concentration of CM used was optimised at 10 $\mu g/ml$.

A549 cells were exposed to asbestos fibres+/−CM for 24 hours before RNA was isolated and reverse transcription performed to yield cDNA for qRT-PCR analysis. Samples were analysed for EGR1 and IL-8 expression using Applied Biosystems reagents and instruments. Gene expression was normalised to 18S ribosomal RNA in control and sample groups to generate fold-change in expression values.

The qRT-PCR protocol used was as follows:

1) Seed cells into 24 well plate ($8 \times 10^4$ cells in 1 ml/well) or T25 ($1 \times 10^6$ cells in 5 ml medium) and allow to adhere overnight.

2) Remove media and add crocidolite/CM in fresh media. Expose cells to asbestos for 24 hours.

3) Remove media and wash cell monolayer with PBS.

4) Add Trizol—100 μl/well for 24-well plate or 1 ml/T25 flask. Cells will lyse and detach.

5) Transfer Trizol to an eppendorf tube. Add 200 μl chloroform and shake vigorously for 1 minute.

6) Proceed with RNA extraction according to Trizol manufacturer's protocol.

7) Resuspend RNA in 40 μl RNAse free water.

8) Quantify RNA yield in nanodrop at A260/230

9) Perform reverse transcription according to manufacturers protocol (use High Capacity cDNA Reverse Transcription Kit from Applied Biosystems #) A total of 2 ug RNA per reaction is optimal.

10) Store cDNA at −20° C. and remaining RNA at −80° C.

11) Perform qRT-PCR using 1.5 μl cDNA/reaction. Samples are amplified using Taqman Gene Expression Master Mix (Applied Biosystems #4369016) with the following:

| | |
|---|---|
| 1.5 μl | Primers |
| 10 μl | Master Mix |
| 1.5 μl | cDNA |
| 7.5 μl | water |

Conclusions

Figure 10:
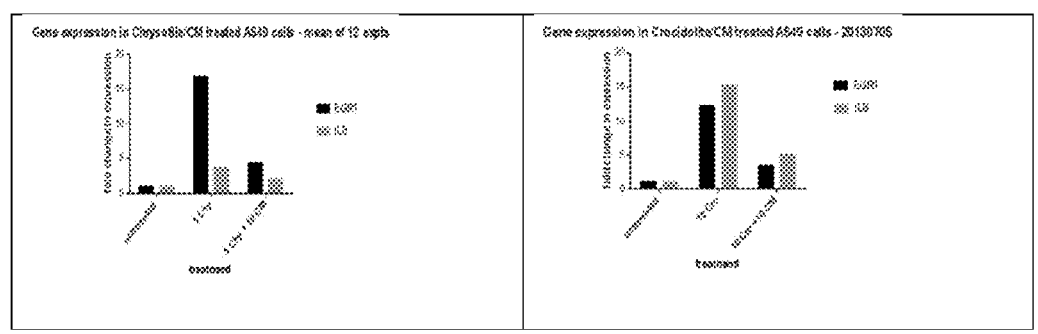
FIG. 10: Left—gene expression in chrysotile/CM treated with A549 cells (mean of 12 experiments). Right—gene expression in crocidolite/CM treated with A549 cells (mean of 12 experiments).

FIG. 10 demonstrates the results (mean of 12 experiments). Both chrysotile and crocidolite increase expression of EGR1 relative to untreated A549 cells, 16.7% and 12.3% respectively. Chrysotile-induced IL-8 expression increases 3.7% while exposure to crocidolite increases IL-8 expression 15.3% relative to untreated controls.

When cells were co-treated with CM and asbestos fibres, increases in expression of both EGR-1 and IL-8 were significantly diminished indicating a protective effect of CM on alterations to asbestos-induced gene expression.

Example 5—Effect of Asbestos and CM on DNA

Typically, cellular chromosomal DNA is rapidly subjected to degradation into much smaller fragments from asbestos fibre exposure. DNA fragmentation was clearly observed in DNA samples treated with very small doses of white or blue asbestos fibres. However, a dramatic preventative improvement was observed, that is, a lack of extensive degradation, in fibre-treated cells that were simultaneously treated with the same dose of CM. At a 10 times lower concentration of CM versus asbestos fibres, the DNA protective effect was as pronounced as seen in the first experiment. The results are shown in FIG. 11.

Example 6—SV40 Immunohistochemistry

Background

MexTAg transgenic mice express the SV40 large T antigen specifically in mesothelial cells by use of the cell-type-specific mesothelin promoter. When exposed to asbestos, these mice develop cancers at 100% incidence that faithfully replicate key features of the pathogenesis of human mesothelioma.

Materials and Methods
1. Deparaffinize sections: xylene 2×5 min, 100% ethanol 2×5 min.
2. 0.8% $H_2O_2$—methanol treatment (add 2 ml 30% $H_2O_2$ to 75 ml methanol) (to block endogenous peroxydase) 30 min.
3. Rehydrate sections successively in 96%-70%-50%-30% ethanol (2 min each) followed by 2 min in PBS.
4. Antigen retrieval: Bath sections in sodium citrate buffer (10 mM, pH 6.0) for 20 min in a water bath at 98° C.
5. Cool sections in citrate buffer for 30 min to RT.
6. Wash sections in PBS 2×10 min.
7. Cover sections with 5% normal horse serum (Vector Laboratories: S-2000) in PBS for 20 min in moist chamber at 37° C.
8. Remove normal serum by tilting (do not rinse).
9. Incubate with the primary antibody (mouse-anti-SV40 pab101, Santa Cruz sc-147, dilution: 1:100) in moist chamber at 4° C. overnight.
10. Remove primary antibody by tilting.
11. Wash sections in PBS 2×5 min.
12. Apply link antibody: Biotinylated horse-anti-mouse IgG (Vector Laboratories: BA-2000) in PBS (1:100) 40 min at 37° C.
13. Wash sections in PBS (1:10) 2×5 min.
14. Incubate with Avidin-Biotin-Enzyme Complex (ABC ELITE Standard, VECTOR: PK-6100) in PBS (1:100) for 30 min. (make ABC 30 min prior to use).
15. Wash sections in Tris-HCl (0.05 M, pH 7.2) for 5 min.
16. Incubate with DAB (diaminobenzidine) in Tris-HCl (0.05M, pH 7.2) for 1-2 min. [Dissolve 100 mg DAB in 10 ml distilled water (2-3 drops 10N HCl) to make stock solution, add 5 ml DAB stock solution in 100 ml Tris-HCl. Just prior to use, add 30 μl 30% $H_2O_2$].
17. Rinse in distilled water three times.
18. Counter-stain in Mayer's hematoxylin for 20 s.
19. Rinse in tap water 5 min.
20. Dehydrate sections successively in 70%-96%-100% ethanol (2×10 sec each), followed by xylene (2×2 min).
21. Embed sections in DEPEX.

SV-40 antigen detection is by staining to a yellow-brown colour. Slides were photographed under 40× and 100× magnifications.

Results

Figure 12:
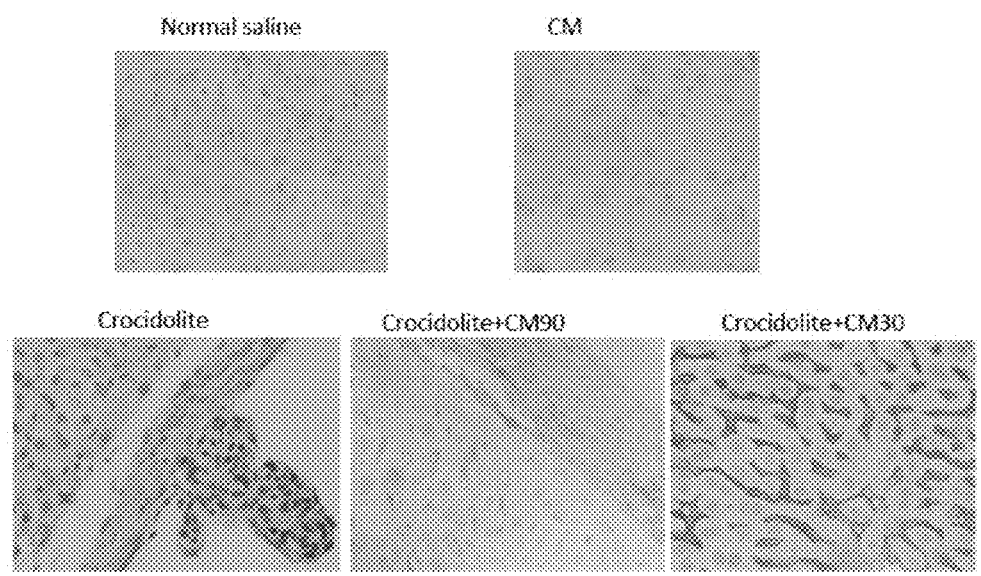
FIG. 12: SV40 immunohistochemistry results of mice that received asbestos in Example 6 (×40).
Figure 13:
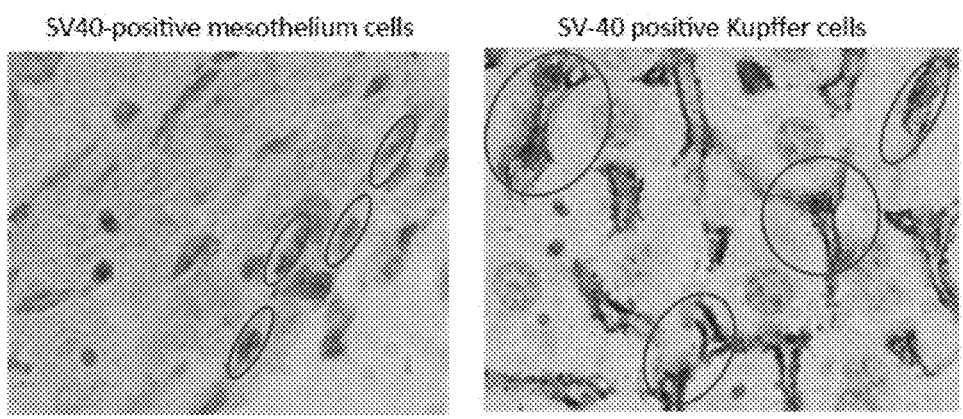
FIG. 13: SV40 immunohistochemistry results of mice that received asbestos in Example 6 (×100).
Figure 14:
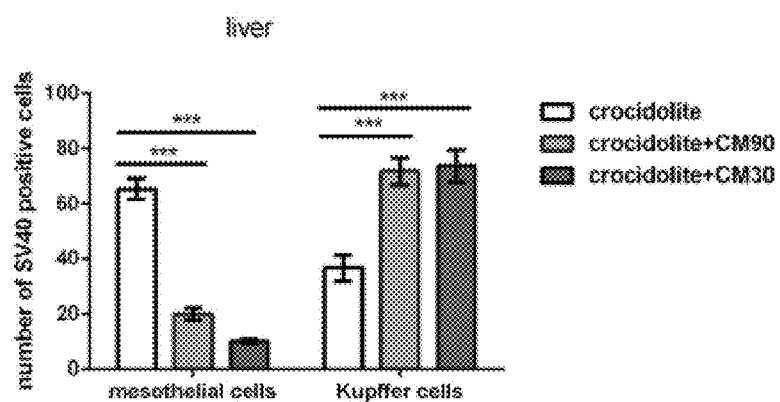
FIG. 14: Plot of the number of SV40 positive cells in the mouse groups that received crocidolite and crocidolite and CM in Example 6.

As expected, there was no SV-40 expression in either saline or CM treated mice (see FIG. 12). After asbestos treatment, SV-40 (brown stained) was seen mainly inside the thickened liver peritoneum, especially in the nuclei of mesothelial cells, and in the cytoplasm of some Kupffer cells in the liver tissue (see FIG. 13). Note, the thickened liver peritoneum is only observed in the asbestos-treated mice, perhaps indicating an inflammatory response and swelling of the peritoneum of epithelial and mesothelial layers. No such swelling occurred in the asbestos+CM mice, which was reflected in the lower numbers of SV40+ mesothelial cells.

In the asbestos+CM30 and asbestos+CM90 treated mice, there was stronger SV40 expression inside Kupffer cells, but less SV-40 in the peritoneum since hardly any thickened peritoneum can be seen in the liver tissues from these mice.

The enhanced SV-40 expression seen in the Kupffer cells from asbestos+CM treated mice might be explained by the phagocytotic effect. The detection of SV40 antigen in liver mesothelial cells is evidence that these cells are likely to develop into mesotheliomas. There is a clear absence of SV40 antigen in the asbestos+CM mice, probably because Kupffer cells have removed any SV40 positive mesothelial cells by phagocytosis, resulting in the detection of SV40 only in the cytoplasm of Kupffer cells. In the slides, the SV40 staining is more prominent in the Kupffer liver macrophages than in the mesothelial cells. Since both are visualised at the same magnification, the difference is clearly due to the much larger size of macrophage versus mesothelial cells.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps, features, compositions and compounds.

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endevour to which this specification relates.

The invention claimed is:

1. A method for treating or preventing mesothelioma, asbestosis, or asbestos-related lung cancer in a subject, the method comprising administration to the subject of an effective amount of a zeolite or a zeolite like material selected from the group consisting of amicite, analcime, barrerite, bellbergite, bikitaite, boggsite, brewsterite, chabazite, clinoptilolite, cowlesite, dachiardite, direnzoite, edingtonite, epistilbite, faujasite, florkeite, ferrierite, garronite, gismondine, gmelinite, gobbinsite, gonnardite, goosecreekite, harmotome, herschelite, heulandite, laumontite, leucite, kalborsite, levyne, maricopaite, mazzite, merlinoite, mesolite, montesommaite, mordenite, mutinaite, natrolite, offretite, paranatrolite, paulingite, pentasil, perlialite, phillipsite, pollucite, scolecite, stellerite, stilbite, svetlozarite, tetranatrolite, thomsonite, terranovaite, tschernichite, tschortnerite, wairakite, wenkite, wellsite, willhendersonite, and yugawaralite, and combinations thereof;

wherein as a result of the administration of the zeolite, progression of the meothelioma, asbestosis, or asbestos-related lung cancer is retarded, hindered, arrested, or reversed in the subject.

2. The method of claim 1, wherein the method is a method for preventing mesothelioma, asbestosis, or asbestos-related lung cancer in a subject.

3. The method of claim 2, wherein the subject is a subject who is deemed to be at risk of developing mesothelioma, asbestosis, or asbestos-related lung cancer.

4. The method of claim 3, wherein the zeolite is administered before first exposure and during exposure to asbestos.

5. The method of claim 1, wherein the method is a method for treating mesothelioma, asbestosis, or asbestos-related lung cancer in a subject.

6. The method of claim 1, wherein the zeolite is administered in the form of microparticles.

7. The method of claim 1, wherein the zeolite is capable of binding, entrapping, or scavenging Fe ions.

8. The method of claim 1, wherein the zeolite is selected from the group consisting of: chabazite, clinoptilolite, ferrierite, boggsite, mordenite, faujasite or any combination thereof.

9. The method of claim 8, wherein the zeolite is clinoptilolite or chabazite.

10. The method of claim 1, wherein the zeolite is administered parenterally or via inhalation.

11. A method for minimizing or modulating asbestos-induced changes in expression of EGR1 or IL-8 in a subject, the method comprising administration to the subject of an effective amount of a zeolite selected from the group consisting of amicite, analcime, barrerite, bellbergite, bikitaite, boggsite, brewsterite, chabazite, clinoptilolite, cowlesite, dachiardite, direnzoite, edingtonite, epistilbite, fauiasite, florkeite, ferrierite, garronite, gismondine, gmelinite, gobbinsite, gonnardite, goosecreekite, harmotome, herschelite, heulandite, laumontite, leucite, kalborsite, levyne, maricopaite, mazzite, merlinoite, mesolite, montesommaite, mordenite, mutinaite, natrolite, offretite, paranatrolite, paulingite, pentasil, perlialite, phillipsite, pollucite, scolecite, stellerite, stilbite, svetlozarite, tetranatrolite, thomsonite, terranovaite, tschernichite, tschortnerite, wairakite, wenkite, wellsite, willhendersonite, and yugawaralite, and combinations thereof;

wherein as a result of administration of the zeolite, expression of EGR1 and/or IL-8 is increased in the subject.

12. The method of claim 11, wherein the changes in expression are an increase in expression.

13. The method of claim 11, wherein the subject is a subject who currently has, or has previously had, or is at risk of, exposure to asbestos.

* * * * *